(12) United States Patent
Hirano et al.

(10) Patent No.: US 9,103,801 B2
(45) Date of Patent: Aug. 11, 2015

(54) DEVICE FOR DETECTING DEFECT OF TURBINE ROTOR BLADE AND METHOD FOR DETECTING DEFECT OF TURBINE ROTOR BLADE

(75) Inventors: Atsuya Hirano, Hitachinaka (JP); Akira Nishimizu, Tokai (JP); Takeshi Kudo, Hitachinaka (JP)

(73) Assignee: Mitsubishi Hitachi Power Systems, Ltd., Kanagawa (JP)

( * ) Notice: Subject to any disclaimer, the term of this patent is extended or adjusted under 35 U.S.C. 154(b) by 485 days.

(21) Appl. No.: 13/124,092

(22) PCT Filed: Oct. 14, 2008

(86) PCT No.: PCT/JP2008/068587
§ 371 (c)(1),
(2), (4) Date: May 18, 2011

(87) PCT Pub. No.: WO2010/044139
PCT Pub. Date: Apr. 22, 2010

(65) Prior Publication Data
US 2011/0218741 A1    Sep. 8, 2011

(51) Int. Cl.
  *G01B 7/00*  (2006.01)
  *G01N 27/82*  (2006.01)
  *G01N 27/90*  (2006.01)

(52) U.S. Cl.
  CPC .......... *G01N 27/9006* (2013.01); *G01N 27/902* (2013.01)

(58) Field of Classification Search
  CPC ..... G01N 27/90; G01N 27/902; G01N 27/82; G01N 2291/2693; G01N 27/9006; F01D 21/003; F01D 17/02; F01D 21/045; F05D 2260/80

USPC .................. 702/38, 34, 35, 59; 324/238, 262
See application file for complete search history.

(56) References Cited

U.S. PATENT DOCUMENTS 4,139,822 A    2/1979  Urich et al.
4,518,917 A    5/1985  Oates et al.
(Continued)

FOREIGN PATENT DOCUMENTS

EP    0 907 077 A2    4/1999
JP    59-98325 U      7/1984
(Continued)

OTHER PUBLICATIONS

Hiroyuki Fukutomi, et al., "Development of Eddy-Current Nondestructive Testing Equipment for Cracks in Land-Based Gas Turbine", Central Research Institute of Electric Power Industry, pp. 53-55.
(Continued)

*Primary Examiner* — Eliseo Ramos Feliciano
*Assistant Examiner* — Yoshihisa Ishizuka
(74) *Attorney, Agent, or Firm* — Crowell & Moring LLP

(57) ABSTRACT

In a defect detection device for a turbine rotor blade, a recess is provided in a side surface of a web provided to the inner circumferential side of a stationary blade diaphragm where stationary blades are annularly arranged adjacent to turbine rotor blades. An eddy current probe is movably installed in the recess, and a rod provided with a signal line for transmitting a signal detected by the eddy current probe, connected to the eddy current prove, is set up to be movable through a hole in a turbine casing and an air gap formed in the stationary blade diaphragm. The eddy current probe is moved toward or away from the turbine rotor blade implanting portion, and a data analyzer determines the condition of a defect occurred in the turbine rotor blade implanting portion based on the signals detected by the eddy current probe.

19 Claims, 9 Drawing Sheets

(56) References Cited

U.S. PATENT DOCUMENTS

| | | | |
|---|---|---|---|
| 4,741,203 A | 5/1988 | Willaman et al. | |
| 5,442,285 A | 8/1995 | Zombo et al. | |
| 5,781,007 A | 7/1998 | Partika et al. | |
| 6,952,094 B1* | 10/2005 | Viertl | 324/238 |
| 2002/0071763 A1* | 6/2002 | Brandl et al. | 415/173.2 |
| 2003/0222640 A1 | 12/2003 | Twerdochlib et al. | |
| 2004/0169510 A1* | 9/2004 | Fields et al. | 324/262 |
| 2006/0017434 A1* | 1/2006 | Tenley et al. | 324/238 |
| 2008/0079426 A1 | 4/2008 | Suzuki et al. | |
| 2010/0085042 A1 | 4/2010 | Suzuki et al. | |
| 2010/0085043 A1 | 4/2010 | Suzuki et al. | |

FOREIGN PATENT DOCUMENTS

| | | |
|---|---|---|
| JP | 7-280773 A | 10/1995 |
| JP | 2002-303103 A | 10/2002 |
| JP | 2003-294716 A | 10/2003 |
| JP | 2004-264305 A | 9/2004 |
| JP | 2005-77320 A | 3/2005 |
| JP | 2006-177941 A | 7/2006 |
| JP | 2008-89328 A | 4/2008 |
| SU | 805097 A1 | 2/1981 |

OTHER PUBLICATIONS

International Search Report dated Jan. 20, 2009 with English translation.

Supplemental European Search Report dated Jun. 26, 2014 (Seven (7) pages).

* cited by examiner

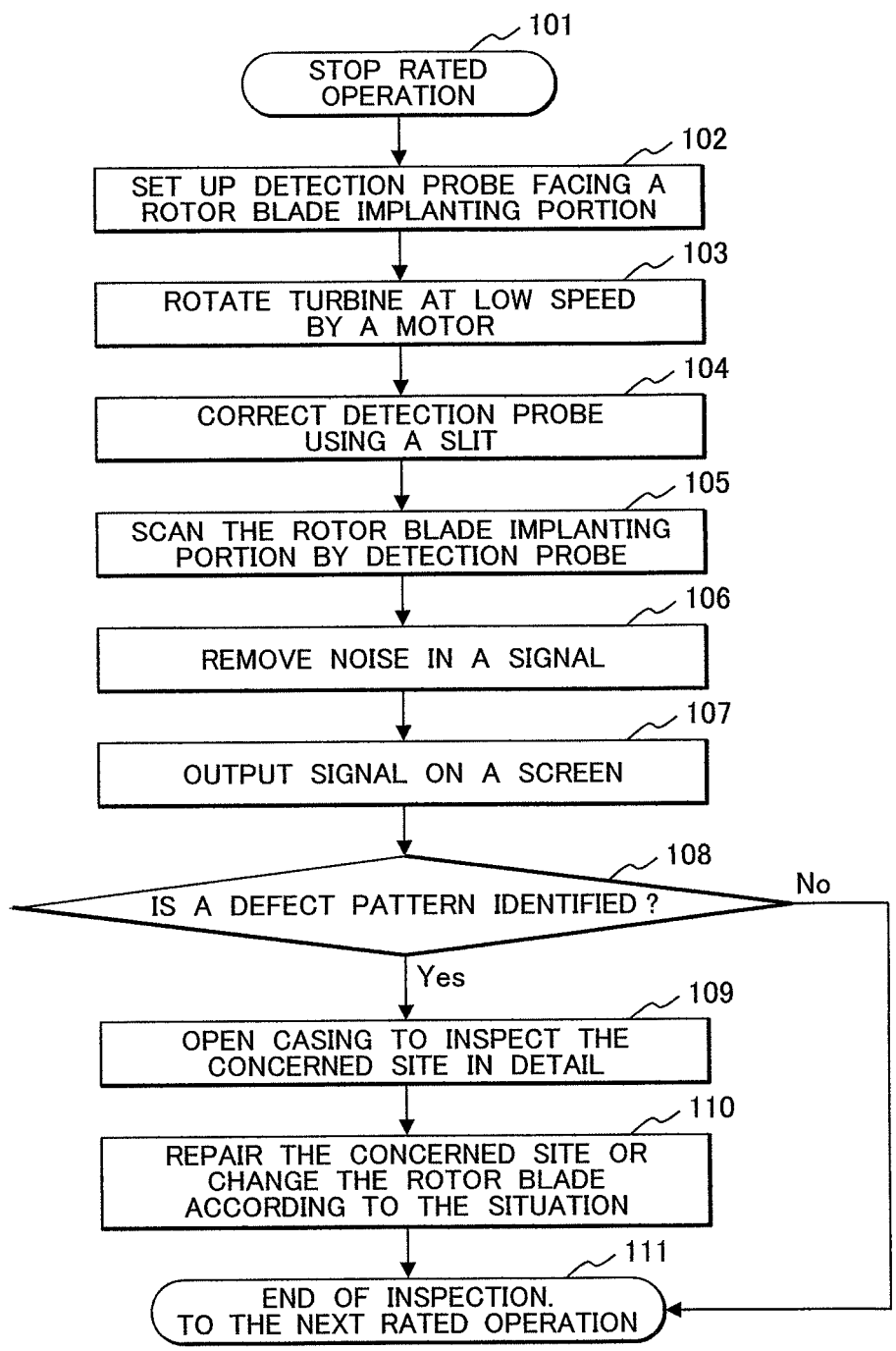

DEVICE FOR DETECTING DEFECT OF TURBINE ROTOR BLADE AND METHOD FOR DETECTING DEFECT OF TURBINE ROTOR BLADE

TECHNICAL FIELD

The present invention relates to technologies for detecting a defect of a turbine rotor blade in a steam turbine and, in particular, to a defect detection device for a turbine rotor blade and a method for detecting a defect of a turbine rotor blade that can occur in a portion for implanting a turbine rotor blade.

BACKGROUND ART

Japanese Patent Laid-Open No. 2003-294716 discloses a technology for detecting a defect in the installation site of turbine blades in which, an echography probe is installed to a turbine blade mounted on a turbine rotor, the installation site of the turbine blades is inspected using the echography probe, and when no defect is detected by the echography, part of the turbine blades are removed from the turbine rotor to perform a magnetic particle inspection or a liquid penetrant inspection having a lower defect detection limit than the echography.

Japanese Utility Model Laid-Open No. Sho 59(1984)-98325 discloses a technology for accurately measuring the vibration of turbine rotor blades in which, the vibration of turbine blades mounted on the wheel of a turbine rotor is detected by a distortion detector provided to the turbine rotor blade, a signal of the vibration of the turbine rotor blades detected by the distortion detector is FM-converted and transmitted from a transmitter provided to the wheel of the turbine rotor, and is received by a receiver provided to a stationary body of the turbine facing the transmitter.

Japanese Patent Laid-Open No. Hei 7(1995)-280773 discloses a technology for detecting a crack in the surface of an air separator, which is a rotating member, by an eddy current sensor installed to a torque tube housing of a combustion turbine engine using a supporting/positioning means.

Patent document 1: Japanese Patent Laid-Open No. 2003-294716

Patent document 2: Japanese Utility Model Laid-Open No. Sho 59(1984)-98325

Patent document 3: Japanese Patent Laid-Open No. Hei 7(1995)-280773

DISCLOSURE OF THE INVENTION

Problems to be solved by the Invention

The above-described technology stated in Japanese Patent Laid-Open No. 2003-294716, however, has a problem that, in order to precisely detect a defect in a rotor blade implanting portion of the turbine rotor blade, a turbine casing of the steam turbine must be removed and opened periodically to pull out the turbine rotor blade to be inspected from the turbine rotor to detect the presence of a defect in the rotor blade implanting portion of the turbine rotor blade, which requires a great deal of time and work to remove the turbine casing and to pull out the turbine rotor blade.

Since the turbine must be paused to remove the turbine casing and to pull out the turbine rotor blade, the defect detection in the rotor blade implanting portion of the turbine rotor blade can be performed only during a periodic inspection.

In the technology stated in Japanese Utility Model Laid-Open No. Sho 59(1984)-98325, the vibration of the turbine blades can be monitored during turbine rotation by the distortion detector mounted on the turbine rotor blade; however, since the distortion detector is mounted onto the rotating turbine rotor blade and the transmitter is installed to the wheel of the turbine rotor, centrifugal force from the rotations of the turbine rotor blades and the turbine rotor may have a harmful effect on the accuracy of the distortion detector, and the installations of the distortion detector and the transmitter may cause the turbine rotor blades to rotate out of balance.

In the technology stated in Japanese Patent Laid-Open No. Hei 7(1995)-280773 for detecting a crack that can occur in the turbine rotor blade implanting portion of the combustion turbine using the eddy current sensor for detecting a crack in the surface of the air separator, which is a rotating body, the rotating turbine rotor blades vibrate in the axial direction of the rotor as the rotor rotates, thus the gap between the eddy current sensor and the turbine rotor blade implanting portion will noticeably fluctuate, which might cause the eddy current sensor to rub up against the turbine rotor blade implanting portion.

There is another problem that, if the eddy current sensor is installed far away from the turbine rotor blade implanting portion to avoid touching the turbine rotor blade implanting portion, it may not be able to accurately detect a defect such as a crack occurred in the turbine rotor blade implanting portion.

An object of the present invention is to provide a defect detection device for a turbine rotor blade and a method for detecting a defect of a turbine rotor blade which can accurately detect a defect occurring in the turbine rotor blade implanting portion even when the turbine rotor blades vibrate in the axial direction of the rotor as the rotor rotates, and can detect a defect occurring in the turbine rotor blade implanting portion to be inspected without opening the turbine casing which requires a great deal of time and work.

Means for Solving the Problems

According to one aspect of the present invention, there is provided a defect detection device for a turbine rotor blade having a turbine rotor blade implanting portion constructed by fitting a set of rotor grooves formed on a rotor disc portion of a turbine rotor and a set of blade grooves formed on a root portion of the turbine rotor blade, wherein the turbine rotor is rotatably installed inside a turbine casing, and around the outer circumference of which turbine rotor, a plurality of turbine rotor blades are annularly arranged, and a stationary blade diaphragm where a plurality of stationary blades are annularly arranged adjacent to the turbine rotor blades, is provided with an annular web in the inner circumference side thereof, and the outer circumference side thereof is fixed with the turbine casing, comprising: a movable eddy current probe for inspecting the state of the turbine rotor blade implanting portion, installed in a recess provided in a side surface of the web of the stationary blade diaphragm, facing the turbine rotor blade implanting portion; a rod provided with a signal line for transmitting a signal detected by the eddy current probe, connected to the eddy current probe, and set up to be movable through a hole formed in the turbine casing and an air gap formed in the stationary blade of the stationary blade diaphragm to move the eddy current probe connected to the rod toward or away from the turbine rotor blade implanting portion; and a data analyzer for determining the condition of the defect occurred in the turbine rotor blade implanting portion based on the detection signal of the turbine rotor blade implanting portion detected by the eddy current probe transmitted through the rod.

According to another aspect of the present invention, there is provided a defect detection device for a turbine rotor blade having a turbine rotor blade implanting portion constructed by fitting a set of rotor grooves formed on a rotor disc portion of a turbine rotor with a set of blade grooves formed on a root portion of the turbine rotor blade, wherein the turbine rotor is rotatably installed inside a turbine casing and around the outer circumference of which turbine rotor, a plurality of turbine rotor blades are annularly arranged, and a stationary blade diaphragm where a plurality of stationary blades are annularly arranged adjacent to the turbine rotor blades, is provided with an annular web in an inner circumference side thereof, and the outer circumference side thereof is fixed with the turbine casing, comprising: an eddy current probe for detecting the state of the turbine rotor blade implanting portion; a groove portion for inserting the eddy current probe, provided on the side surface of the web of the stationary blade diaphragm facing the turbine rotor blade implanting portion, opened toward a radial direction of the stationary blade diaphragm, having a tapered surface on the bottom surface thereof for making the groove shallower toward a rotor shaft, the tapered surface abuts on other tapered surface corresponding to the tapered surface formed on the bottom surface of the groove portion, the other tapered surface formed on a stationary blade diaphragm side of the eddy current probe is to move the eddy current probe toward or away from the turbine rotor blade implanting portion by the sliding action of these tapered surfaces; a rod provided with a signal line for transmitting a signal detected by the eddy current probe, connected to the eddy current probe, and set up to be movable through a hole formed in the turbine casing and a space between the stationary blades installed in the stationary blade diaphragm to move the eddy current probe connected to the rod toward or away from the turbine rotor blade implanting portion; and a data analyzer for determining a condition of the defect occurred in the turbine rotor blade implanting portion based on the detection signal of the turbine rotor blade implanting portion detected by the eddy current probe transmitted through the rod.

According to still another aspect of the present invention, there is provided a method for detecting a defect of a turbine rotor blade having a turbine rotor blade implanting portion constructed by fitting a set of rotor grooves formed on a rotor disc portion of a turbine rotor with a set of blade grooves formed on each root portion of a plurality of turbine rotor blades annularly arranged around the outer circumference of the turbine rotor rotatably installed in a turbine casing, comprising: movably setting up an eddy current probe in a recess formed on a side surface of a web facing the turbine rotor blade implanting portion, the web is among those provided to the inner circumference side of a stationary blade diaphragm where a plurality of stationary blades are annularly arranged; operating a rod provided with a signal line for transmitting a signal detected by the eddy current probe, connected to the eddy current probe, from outside of the turbine casing to move through a hole formed in the turbine casing and an air gap formed in the stationary blade of the stationary blade diaphragm when the state of the defect in the turbine rotor blade implanting portion is to be inspected; moving the eddy current probe connected to the moving rod toward or away from the turbine rotor blade implanting portion to inspect the state of the turbine rotor blade implanting portion using the eddy current probe, and determining the condition of the defect occurred in the turbine rotor blade implanting portion based on the detection signal of the state of the turbine rotor blade implanting portion detected by the eddy current probe transmitted through the rod.

According to still another aspect of the present invention, there is provided a method for detecting a defect of a turbine rotor blade having a turbine rotor blade implanting portion constructed by fitting a set of rotor grooves formed on a rotor disc portion of a turbine rotor with a set of blade grooves formed on each root portion of a plurality of turbine rotor blades annularly arranged around the outer circumference of the turbine rotor rotatably installed in a turbine casing, comprising: removably setting up an eddy current probe in a groove portion formed on the side surface of a web, facing the turbine rotor blade implanting portion, opened toward a radial direction of a stationary blade diaphragm, the web is among those provided to the inner circumference side of the stationary blade diaphragm where a plurality of stationary blades are annularly arranged; inserting a rod provided with a signal line for transmitting a signal detected by the eddy current probe, connected to the eddy current probe, from outside of the turbine casing to move through a hole formed in the turbine casing and a space between the stationary blades installed in the stationary blade diaphragm when a state of the defect in the turbine rotor blade implanting portion is to be inspected; inserting the eddy current probe connected to the moving rod into the groove portion formed on the side surface of the web of the stationary blade diaphragm and positioning the eddy current probe closer to the turbine rotor blade implanting portion to inspect the state of the turbine rotor blade implanting portion using the eddy current probe; and determining the condition of the defect occurred in the turbine rotor blade implanting portion based on the detection signal of the state of the turbine rotor blade implanting portion detected by the eddy current probe transmitted through the rod.

Advantages of the Invention

According to the present invention, a defect detection device for a turbine rotor blade and a method for detecting a defect of a turbine rotor blade can be achieved which can accurately detect a defect occurred in the turbine rotor blade implanting portion even when the turbine rotor blades vibrate in the axial direction of the rotor as the rotor rotates, and can detect a defect occurred in the turbine rotor blade implanting portion to be inspected without opening the turbine casing which requires a great deal of time and work.

BRIEF DESCRIPTION OF DRAWINGS

FIG. 4 is a flow chart showing the inspection procedures for detecting a defect in the implanting portion of the turbine rotor blade provided to the steam turbine, using the defect detection device of turbine rotor blade according to the embodiment of the present invention.

LEGEND

1: a steam turbine, 2: a turbine casing, 3: a turbine rotor, 4: a turbine rotor blade, 5: a stationary blade diaphragm, 6: a rotor blade implanting portion, 7: a defect detection device, 8: result output, 31: a rotor shaft, 32: a rotor disc, 33: a set of rotor grooves, 41: a rotor blade, 42: a set of blade grooves, 51: a ring, 52: a stationary blade, 53: an annular element referred to elsewhere in this disclosure as a "web," 61: a crack, 68: a fixing groove, 69: an opening portion, 71 and 71a: an eddy current probe, 72: a fiber rod, 72a: an access rod, 73: a recess, 74: a web hole, 75: an air gap, 76: a casing hole, 77 and 77a: a guide roller, 78: a coil element, 81: an indication, 82: an indication, 91: a coil spring, 92: a cable, 93: a sliding pad, 94: an aerodynamic blade, 107: a tapered surface, 71a: a cushion, 150: a moving device, 200: a control device, 300: a data analyzer.

BEST MODES FOR CARRYING OUT THE INVENTION

The defect detection device of turbine rotor blade and the method for detecting defect of turbine rotor blade according to various embodiments of the present invention will be described next with reference to the drawings.

Embodiment 1

The defect detection device for a turbine rotor blade and the method for detecting a defect of a turbine rotor blade according to a first embodiment of the present invention will be described with reference to FIGS. 1 to 5.

Figure 1A:
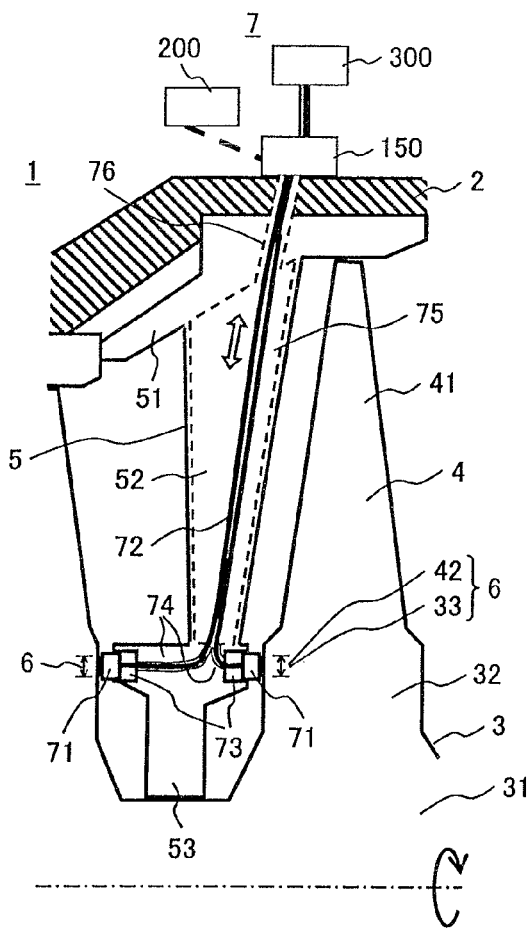
FIG. 1 shows a structural view of an eddy current probe constituting a defect detection device for a turbine rotor blade according to a first embodiment of the present invention, and partial cross-sectional views of a steam turbine installed with the defect detection device of turbine rotor blade.

FIG. 1A is a partial cross-sectional view of a steam turbine installed with the defect detection device of turbine rotor blade according to the first embodiment of the present invention.

In FIG. 1A, a steam turbine 1 has a turbine rotor 3 in a turbine casing 2 covering the outer circumference of the turbine, a plurality of turbine rotor blades 4 annularly arranged around the outer circumference of the turbine rotor 3, each having a rotor blade 41, and a stationary blade diaphragm 5 adjacently disposed in the upstream side of the plurality of annularly arranged turbine rotor blades 4, having a plurality of annularly arranged stationary blades 52.

Although FIG. 1A shows only one turbine stage, which is made up of the stationary blades 52 and the turbine rotor blades 4, for descriptive purposes, a plurality of turbine stages are fixedly set up in the axial direction of the turbine rotor 3.

The turbine rotor 3 has a rotor shaft 31, which is the axis of turbine rotation, an annular rotor disc 32 mounted on the outer circumference of the rotor shaft 31, and a set of rotor grooves 33 formed on the outer circumference of the rotor disc 32 for fitting with a set of blade grooves 42 formed on the root portion of the turbine rotor blade 4 to mount the root portion and to annularly arrange the plurality of turbine rotor blades 4 around the outer circumference of the rotor disc 32 (hereinafter, directions are described as the axial direction, the radial direction, and the circumferential direction with reference to the axis of turbine rotation).

The turbine blades 4 numerously and annularly arranged around the rotor disc 32 each have the rotor blade 41 for receiving a high-pressure steam flow, which is a working fluid, to convert the high-pressure steam flow to the rotation energy of the turbine, and the set of blade grooves 42 formed on the implanting portion of the turbine rotor blade 4 for fitting with the set of rotor grooves 33 formed on the turbine rotor 3.

The joining site where the set of rotor grooves 33 formed on the rotor disc 32 is fitted with the set of blade grooves 42 formed on the root portion of the turbine rotor blade 4 is called a rotor blade implanting portion 6 of the turbine rotor blade 4.

The stationary blade diaphragm 5 is fixedly set up between each turbine rotor blades 4 in the axial direction of the turbine rotor 3, which are multiply installed away from each other.

The stationary blade diaphragm 5 includes a ring 51 fixed to the turbine casing 2 at the outer circumference side of the stationary blade diaphragm 5, a plurality of annularly arranged stationary blades 52 adjacently located in the upstream or the downstream side of the rotor blades 41 of the turbine rotor blades 4, for adjusting the steam flow passed through the rotor blades 41, and an annular web 53 adjacent to the rotor disc 32 and the rotor blade implanting portion 6 of the turbine rotor blade 4 in the axial direction of the rotor, set up close to the rotor shaft 31 at the inner circumference side of the stationary blade diaphragm 5. These members are joined together by welding.

A defect detection device of turbine rotor blade 7 according to the first embodiment of the present invention for detecting a defect occurring in the rotor blade implanting portion 6 of the turbine rotor blade while the turbine rotor blades 4 of the stream turbine are rotating at low speed to allow an eddy current probe 71 to inspect the condition of a defect in the rotor blade implanting portion 6 of the turbine blade 4, is installed so as to allow the eddy current probe 71 for detecting a defect occurring in the rotor blade implanting portion 6 of the turbine blade 4 to be moved toward or away from the surface of the rotor blade implanting portion 6 of the turbine blade 4 in the axial direction of the rotor, in a recess 73 formed in the annular web 53 installed at the inner circumference side of the stationary blade diaphragm 5, the recess facing the rotor blade implanting portion 6 of the turbine rotor blade 4.

Figure 1B:
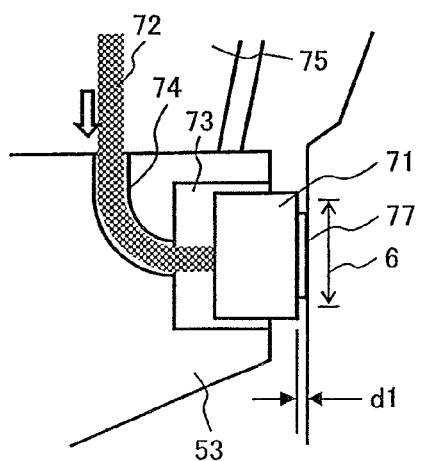

The defect detection device of turbine rotor blade 7 includes the eddy current probe 71 which is installed in the recess 73 formed in the web 53 of the stationary blade diaphragm 5, facing the rotor blade implanting portion 6 of the turbine rotor blade 4 as shown in FIG. 1B, and movable toward or away from the surface of the rotor blade implanting portion 6 of the turbine rotor blade 4 in the axial direction of the rotor; a fiber rod 72, one end of which is connected to the eddy current probe 71, and which is movable forward and backward, fixedly set up to sequentially pass through a web hole 74 provided at the bottom portion of the recess 73 formed in the web 53 of the stationary blade diaphragm 5, an air gap 75 inside the stationary blade 52 provided to the stationary blade diaphragm 5, and a casing hole 76 formed in the ring 51 and the turbine casing 2, and also serves as a signal line for transmitting to the outside of the turbine casing 2 a detection signal of the condition of a defect in the rotor blade implanting portion 6 of the turbine rotor blade 4 measured by the eddy current probe 71 while the turbine rotor blades 4 are rotating at low speed; a moving device 150 installed outside the turbine casing 2 for moving the fiber rod 72 forward and backward; and a data analyzer 300 installed outside the turbine casing 2 for performing calculation based on the detection signals measured by the eddy current probe 71 transmitted through the fiber rod 72, and for displaying the indications of inspection result output 8 for a defect occurring in the rotor blade implanting portion 6 of the turbine rotor blade 4.

Note that the fiber rod 72 may be moved forward and backward by a manual operation from the outside of the turbine casing 2, and in this case, the moving device 150 for moving the fiber rod 72 and a control device 200 for driving the moving device 150 will be unnecessary.

The eddy current probe 71 passes an eddy current to the surface of the rotor blade implanting portion 6 of the turbine blade 4 to detect a change in electromagnetic induction generated in the rotor blade implanting portion 6, and the data analyzer 300 performs calculation based on the change in the electromagnetic induction detected by the eddy current probe 71 to detect the location and the depth of a damage occurred in the rotor blade implanting portion 6.

A rotatable guide roller 77 is installed on the front surface of the eddy current probe 71 to function as a guide so that when the eddy current probe 71 is moved forward or backward in the axial direction of the rotor by the forward moving operation of the fiber rod 72 to inspect the rotor blade implanting portion 6 of the turbine rotor blade 4, the guide roller 77 provided on the front surface of the eddy current probe 71 contacts the surface of the rotor blade implanting portion 6 of the turbine rotor blade 4 rotating around the rotor axis.

The data analyzer 300 analyzes the condition of a defect such as a crack in the rotor blade implanting portion 6 of the turbine rotor blade 4 based on the detection signal of a change in the electromagnetic induction generated in the rotor blade implanting portion 6 of the turbine rotor blade 4 measured by the eddy current probe 71, and displays the location and the depth of the defect.

The eddy current probe 71 is installed one for each of the both ends in the axial direction of the stationary blade diaphragm 5, facing the rotor blade implanting portion 6 of the turbine rotor blade 4 to be inspected.

That is, the eddy current probes 71 are each stored in the recess 73 formed in the either end in the axial direction of the web 53 of the stationary blade diaphragm 5 so as to face the rotor blade implanting portions 6 of the turbine rotor blade 4 located in the downstream side of the stationary blade diaphragm 5 and of the turbine rotor blade 4 (not shown) located in the upstream side of the stationary blade diaphragm 5 respectively.

The detection signal of a change in the electromagnetic induction in the rotor blade implanting portion 6 of the turbine rotor blade 4 detected by passing an eddy current from each eddy current probe 71 to detect a change in the electromagnetic induction generated in the rotor blade implanting portion 6 is transmitted to the data analyzer 300 installed outside the turbine casing 2 through the fiber rod 72 fixedly set up to pass through the web hole 74 provided at the bottom portion of the recess 73 formed in the web 53 of the stationary blade diaphragm 5, the air gap 75 inside the stationary blade 52 provided to the stationary blade diaphragm 5, and the casing hole 76 formed in the ring 51 and the turbine casing 2; and the data analyzer 300 analyzes the condition of a defect such as a crack in the rotor blade implanting portion 6 of the turbine rotor blade 4 to display the location and the depth of the defect.

In addition, the moving device 150 for moving the fiber rod 72 forward or backward in the set up direction, which fiber rod is for moving the eddy current probe 71 forward or backward in the axial direction of the rotor in the recess 73 formed in the web 53 of the stationary blade diaphragm 5, is installed outside the turbine casing 2 to move the eddy current probe 71 toward or away from the surface of the rotor blade implanting portion 6 of the turbine rotor blade 4. The moving device 150 is driven by an operation command from the control device 200.

When the condition of a defect in the rotor blade implanting portion 6 of the turbine rotor blade 4 is to be inspected using the defect detection device 7, as shown in the partially enlarged view of the eddy current probe 71 in FIG. 1B, the moving device 150 installed outside the turbine casing 2 is driven by an operation command from the control device 200 and pushes the fiber rod 72 forward, which makes the eddy current probe 71 connected to the end of the fiber rod 72 to be pushed forward in the axial direction of the rotor from the opening of the recess 73 to be abutted on the surface of the rotor blade implanting portion 6 of the turbine rotor blade 4, so that an eddy current can be passed from the eddy current probe 71 to the surface of the rotor blade implanting portion 6 of the turbine blade 4, and a change in the electromagnetic induction generated in the rotor blade implanting portion 6 can be detected to inspect the condition of a defect in the rotor blade implanting portion 6 of the turbine rotor blade 4.

The guide roller 77 is installed on the front surface of the eddy current probe 71, and when the guide roller 77 of the eddy current probe 71 abuts on the surface of the rotor blade implanting portion 6 of the turbine rotor blade 4 due to the eddy current probe 71 being pushed forward in the axial direction of the rotor, a desirable gap d1 of 0.5 to 1.0 mm, which is optimal for the eddy current probe 71, is formed between the surfaces of the eddy current probe 71 and of the rotor blade implanting portion 6.

The eddy current probe 71 is constructed to allow the guide roller 77 provided on the front surface thereof to abut on the surface of the rotor blade implanting portion 6 of the turbine rotor blade 4, so that even when the rotor blade implanting portion 6 of the turbine rotor blade 4 vibrates in the axial direction of the rotor due to the rotation of the turbine rotor, the gap between the surfaces of the eddy current probe 71 and of the rotor blade implanting portion 6 can always be maintained to the desirable gap d1 of 0.5 to 1.0 mm, allowing the occurrence of a defect in the rotor blade implanting portion 6 of the turbine rotor blade 4 to be accurately detected using the eddy current probe 71.

Figure 1C:
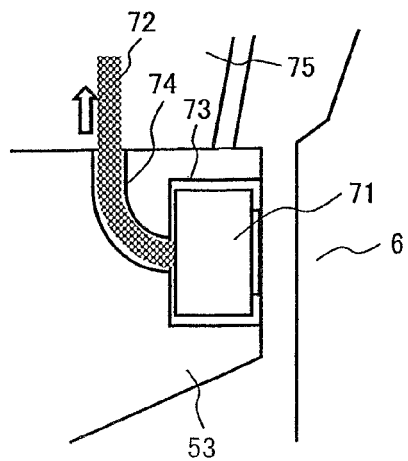

When the rotor blade implanting portion 6 of the turbine rotor blade 4 is not to be inspected, as shown in FIG. 1C, the moving device 150 is driven or the defect detection device is manually operated to pull the fiber rod 72 to move the eddy current probe 71 connected to the fiber rod 72 widely away from the surface of the rotor blade implanting portion 6 of the turbine rotor blade 4, so the eddy current probe 71 is pulled backward in the axial direction of the rotor through the opening of the recess 73 to be stored in the recess 73.

The fiber rod 72 has a bendable flexible structure in the portion corresponding to an L-shaped curved pipe of the web hole 74, but the other portion is rigid to provide appropriate push or pull force to the eddy current probe 71 without causing of buckling when it is being pushed or pulled by the operation of the moving device 150 or by a manual operation.

A cable (not shown) is built in the fiber rod 72 to transmit a detection signal of the condition of a defect in the rotor blade implanting portion 6 of the turbine rotor blade 4 detected by the eddy current probe 71.

Next, the defect detection device of turbine rotor blade for measuring the condition of a defect in the rotor blade implanting portion 6 of the turbine rotor blade 4 will be described in further detail.

Figure 2A:
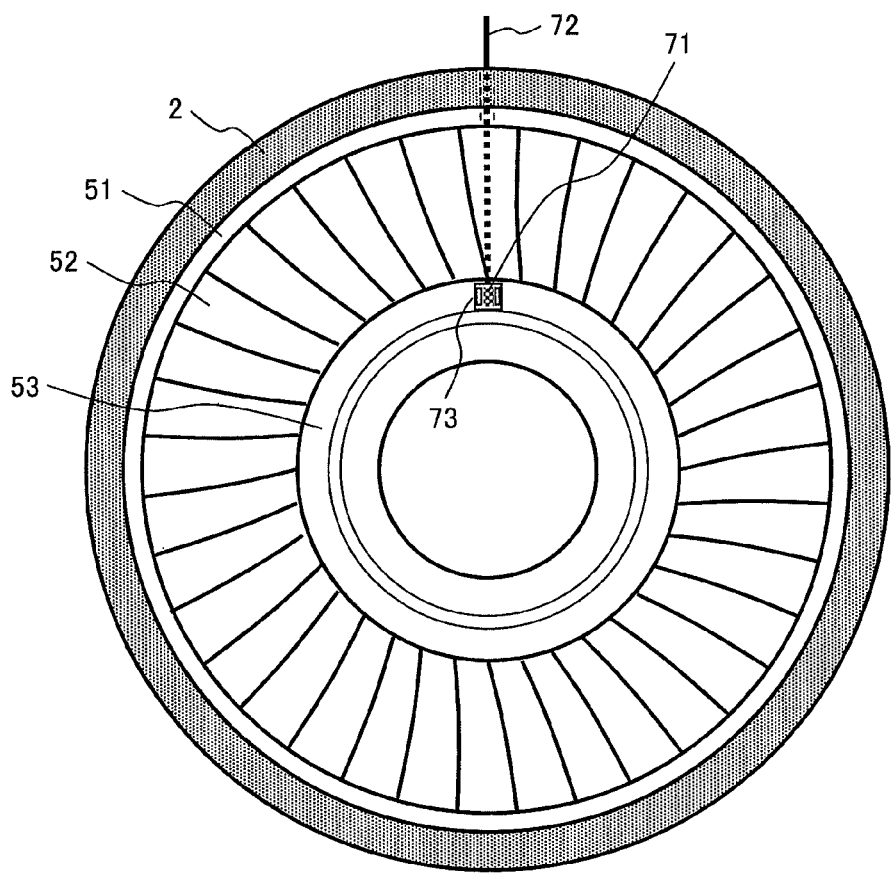
FIG. 2 shows a perspective view of the eddy current probe constituting the defect detection device of turbine rotor blade according to the first embodiment of the present invention shown in FIG. 1, and a schematic structural view of a stationary blade diaphragm installed with the defect detection device of turbine rotor blade, viewed from the axial direction of the turbine rotor.

FIG. 2A is a schematic structural view of the stationary blade diaphragm installed with the defect detection device of turbine rotor blade according to the first embodiment of the present invention shown in FIG. 1, viewed from the axial direction of the turbine rotor.

In FIG. 2A, the eddy current probe 71 constituting part of the defect detection device of turbine rotor blade is provided in each recess 73 formed in an annular region at the both ends in the axial direction of the web 53 installed to the inner circumference side of the stationary blade diaphragm 5, facing the rotor blade implanting portion 6 of the turbine rotor blade 4 to be inspected.

Figure 2B:
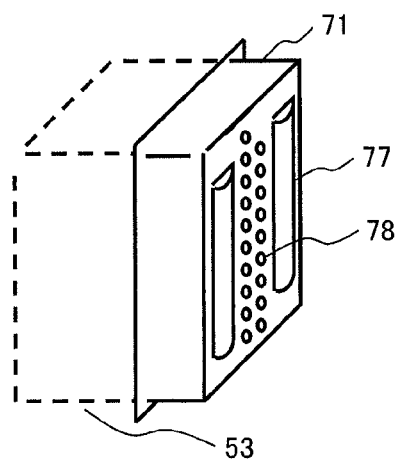

FIG. 2B is a perspective view of the eddy current probe constituting the defect detection device of turbine rotor blade according to the first embodiment of the present invention shown in FIG. 1.

On the front surface of the eddy current probe 71 facing the rotor blade implanting portion 6 of the turbine rotor blade 4 to be inspected, coil elements 78 each including a first coil element for passing an eddy current to the surface of the rotor blade implanting portion 6 of the turbine blade 4 and a second coil element for detecting a change in the electromagnetic induction generated on the surface of the rotor blade implanting portion 6 of the turbine blade 4 by passing the eddy current, are arranged in series in two lines in the radial direction; and the coil elements 78 are fixedly set up on the front surface of the eddy current probe 71 over the length in the radial direction to cover the region to be inspected of the rotor blade implanting portion 6 of the turbine rotor blade 4 with the desirable gap d1 of 0.5 to 1.0 mm maintained between the coil elements 78 on the front surface of the eddy current probe 71 and the surface of the rotor blade implanting portion 6 of the turbine rotor blade 4 when the guide rollers 77 on the front surface of the eddy current probe 71 are abutting on the rotor blade implanting portion 6 of the turbine rotor blade 4 to be inspected.

Two rotatable guide rollers 77 installed on the front surface of the eddy current probe 71 are installed in parallel on the both sides of the coil elements 78, and are each rotatably fixed to its axle (not shown) held inside the eddy current probe 71.

Figure 2C:
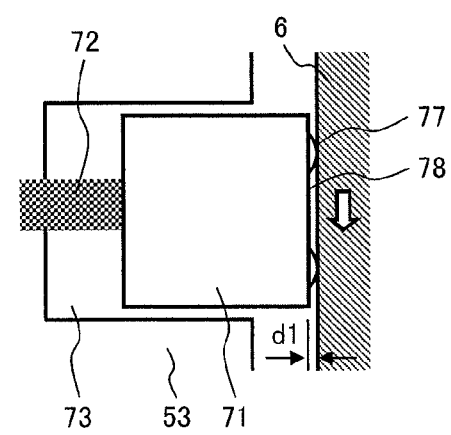

FIG. 2C shows the guide rollers 77 of the eddy current probe 71 abutting on the surface of the rotor blade implanting portion 6 of the turbine rotor blade 4 to be inspected; and when the rotor blade implanting portion 6 of the turbine rotor blade 4 rotates as shown in the arrow, along with the rotation of the turbine rotor blades 4, each guide roller 77 on the front surface of the eddy current probe 71 abutting on the surface of the rotor blade implanting portion 6 also rotates around its axle, providing a smooth sliding on the surface of the rotor blade implanting portion 6 of the turbine rotor blade 4.

Consequently, the gap d1 necessary for detecting a defect occurred in the rotor blade implanting portion 6 can always be maintained between the coil elements 78 installed on the front surface of the eddy current probe 71 and the rotor blade implanting portion 6 of the turbine rotor blade 4 to be inspected, allowing the coil elements 78 of the eddy current probe 71 to scan the surface of the rotor blade implanting portion 6 of the turbine rotor blade 4.

Figure 3A:
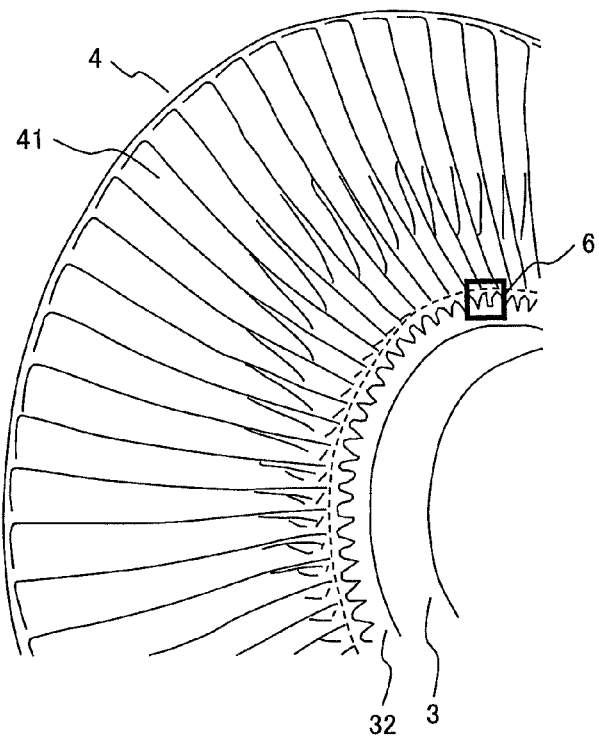
FIG. 3 shows a perspective view of turbine rotor blades showing a turbine rotor blade implanting portion, which is the target of inspection by the defect detection device of turbine rotor blade, according to the first embodiment of the present invention, and partially enlarged views of the rotor blade implanting portion.

FIG. 3A is a perspective view of the turbine rotor blades, showing a rotor blade implanting portion of the turbine rotor blade to be inspected by the defect detection device of turbine rotor blade according to the first embodiment of the present invention.

In FIG. 3A, the turbine rotor blades 4, as described using FIG. 1, are numerously and annularly arranged around the annular rotor disc 32 mounted on the outer circumference of the rotor shaft 31 constituting the turbine rotor 3; and in the rotor blade implanting portion 6 of the turbine rotor blade 4, the set of blade grooves 42 formed on the root portion of the turbine rotor blade 4 is fitted with the set of rotor grooves 33 formed on the outer circumference of the rotor disc 32 to join the turbine rotor blade 4 to the rotor disc 32 of the turbine rotor 3.

Figure 3B:
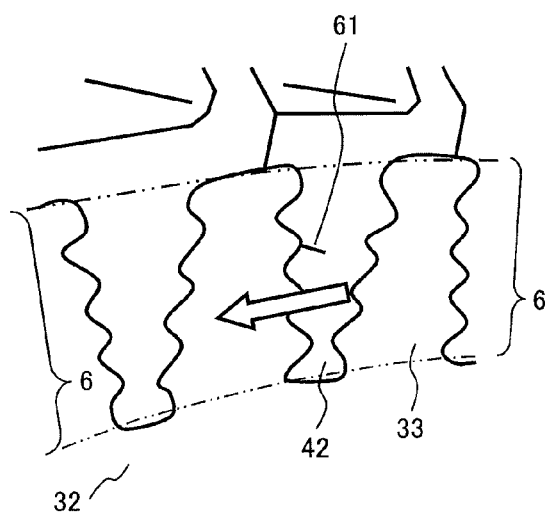

FIG. 3B is a partially enlarged view of the rotor blade implanting portion of the turbine rotor blade shown in FIG. 3A.

In FIG. 3B, the set of blade grooves 42 formed on the root portion of the turbine rotor blade 4, which will constitute the rotor blade implanting portion 6 of the turbine rotor blade 4, has a reversed Christmas tree shape having a plurality of convexes of a zigzag contour, and this set of blade grooves 42 formed on the root portion of the turbine rotor blade 4 rigidly engages with the set of rotor grooves 33 formed on the rotor disc 32 having a shape with a plurality of concaves of a zigzag contour, corresponding to the shape of the set of blade grooves 42 of the turbine rotor blade 4, to be joined together.

When the turbine is rotating under the normal operation of the steam turbine, the turbine rotor blades 4 are affected by centrifugal force in the radial direction as well as vibration loads in the circumferential and the axial directions of the rotor; and since these loads are supported by the above-described engaging structure of the rotor blade implanting portion 6 of the turbine rotor blade 4, significant stress may be locally generated by the loads, affecting the engaging structure of the rotor blade implanting portion 6 of the turbine rotor blade 4 to increase the risk of creating a crack 61.

For example, if a small crack occurs in the engaging structure of the rotor blade implanting portion 6 of the turbine rotor blade 4 and if the small crack occurred is neglected for a long period of time, it may become a larger crack and eventually could end up as a damaging defect to the set of rotor grooves 33 or blade grooves 42 in the engaging structure of the rotor blade implanting portion 6 of the turbine rotor blade 4.

Thus, a small crack occurring in the engaging structure of the rotor blade implanting portion 6 of the turbine rotor blade 4 must be surely detected before it appears as the damaging defect in the implanting portion 6 of the turbine rotor blade 4.

As shown in FIG. 3B, the crack 61 occurred in the engaging structure of the rotor blade implanting portion 6 of the turbine rotor blade 4 has a characteristic to preferentially develop in the axial direction of the rotor even when it has occurred inside the structure in the axial direction of the rotor, so that the crack 61 would first appear on the surface of the rotor blade implanting portion 6 of the turbine rotor blade 4 before the set of rotor grooves 33 formed on the outer circumference of the rotor disc 32 or the set of blade grooves 42 formed on the root portion of the turbine rotor blade 4 constituting the engaging structure of the rotor blade implanting portion 6 of the turbine rotor blade 4 gets damaged.

For this reason, when the crack 61 appears on the surface of the rotor blade implanting portion 6 of the turbine rotor blade 4, the eddy current probe 71 provided to the defect detection device of turbine blade 7, theoretically, can detect a surface defect occurring on the surface of the rotor blade implanting portion 6 of the turbine rotor blade 4.

In the eddy current probe 71 of the defect detection device of turbine blade 7 according to the first embodiment, as shown in FIG. 2B, the coil elements 78 are arranged over the length in the radial direction to cover the inspection target region in the rotor blade implanting portion 6 of the turbine rotor blade 4, on the front surface of the eddy current probe 71.

So, while the rotatable guide rollers 77 installed on the front surface of the eddy current probe 71 where the coil elements 78 are arranged, are abutting on the surface of the rotor blade implanting portion 6 of the turbine rotor blade 4, the rotor blade implanting portion 6 of the turbine rotor blade 4 is rotated as shown in the arrow in FIG. 3B.

Then, an eddy current can be passed by the eddy current probe 71 of the defect detection device 7 to the entire annular region on the surface of the rotor blade implanting portion 6 of the turbine rotor blade 4, as the target of inspection, shown in two-dot chain lines in FIG. 3B, and a change in the electromagnetic induction generated on the surface of the rotor blade implanting portion 6 of the turbine rotor blade 4 can be detected by the eddy current probe 71 to detect the occurrence of a defect.

Figure 3C:
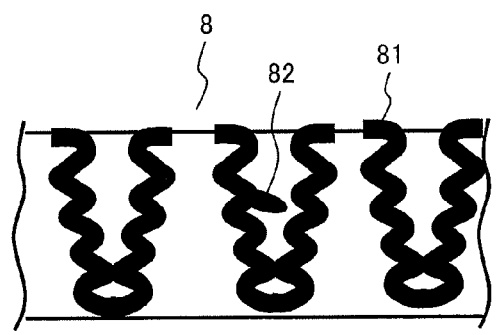

FIG. 3C is an image, displayed on a screen as the inspection result output 8, of a defect identified by calculation in the data analyzer 300 based on the detection signals of the rotor blade implanting portion 6 of the turbine rotor blade 4 detected by the eddy current probe 71 provided to the defect detection device of turbine rotor blade 7 according to the first embodiment.

The above-described eddy current probe 71 can sense a crack of a defect as deep as several millimeters from the surface of the rotor blade implanting portion 6 of the turbine rotor blade 4, thus the crack 61 occurred in the rotor blade implanting portion 6 of the turbine rotor blade 4 obtained by calculation in the dada analyzer 300 based on the detection signals measured by the eddy current probe 71 is displayed on the screen, and in addition, indications 81 corresponding to the set of blade grooves 42 formed on the root portion of the turbine rotor blade 4 and the set of rotor grooves 33 formed on the rotor disc 32 constituting the engaging structure of the rotor blade implanting portion 6 of the turbine rotor blade 4 are also displayed as the inspection result output 8; since these sets of blade grooves 42 and rotor grooves 33 have a certain fixed shape, an indication 82 corresponding to the crack 61 of the defect, which has an irregular shape, can be easily identified.

FIG. 4 is a flow chart showing the procedures for detecting a defect in the rotor blade implanting portion 6 of the turbine rotor blade 4 provided to a steam turbine for thermal power generation, using the defect detection device of turbine rotor blade 7 according to the first embodiment of the present invention.

The steam turbine in the rated operation is rotating at 3000 or 3600 rpm, and a circumferential speed of the rotation of the rotor blade implanting portion 6 of the turbine rotor blade 4 to be inspected in the steam turbine will be more than 100 m/s; at such high speed, a defect in the rotor blade implanting portion 6 of the turbine rotor blade 4 cannot be detected using the eddy current probe 71 provided to the defect detection device 7.

Thus, the defect inspection is performed on the day when the operation of the stream turbine for thermal power generation is shut down or during an operation pause period in every few days.

The inspection for a defect in the rotor blade implanting portion 6 of the turbine rotor blade 4 is performed according to the following procedures.

First, in Step 101, the rated operation of a steam turbine is stopped.

Next, in Step 102, the moving device 150 is driven by a command signal from the control device 200 constituting the defect detection device 7 for the turbine rotor blade 4 to push the fiber rod 72 from the outside of the turbine casing 2, so as shown in FIG. 1B, the eddy current probe 71 is pushed forward in the axial direction of the rotor from the opening of the recess 73 formed in the web 53 of the stationary blade diaphragm 5 to make the guide rollers 77 provided in parallel at the both sides of the coil elements 78 arranged on the front surface of the eddy current probe 71 abut on the surface of the rotor blade implanting portion 6 of the turbine rotor blade 4.

Then, in Step 103, the rotor shaft 31 of the steam turbine 1 is rotated by an external power motor (not shown) to start a low-speed operation in which, the steam turbine 1 is rotated at low speed. In the low-speed operation of the steam turbine 1, the rotor shaft 31 of the steam turbine 1 is rotated at 10 mm/s, which is the circumferential speed of the rotor blade implanting portion 6 of the turbine rotor blade 4 that allows the eddy current probe 71 to detect a defect.

Then, in Step 104, the eddy current probe 71 is corrected. This is done because the sensitivity of the coil elements 78, which are provided on the front surface of the eddy current probe 71 for generating an eddy current on the surface of the rotor blade implanting portion 6 of the turbine rotor blade 4 to detect a change in the electromagnetic induction generated on the surface of the rotor blade implanting portion 6 of the turbine rotor blade 4, can be easily changed over time depending on the measuring environment.

Figure 5:
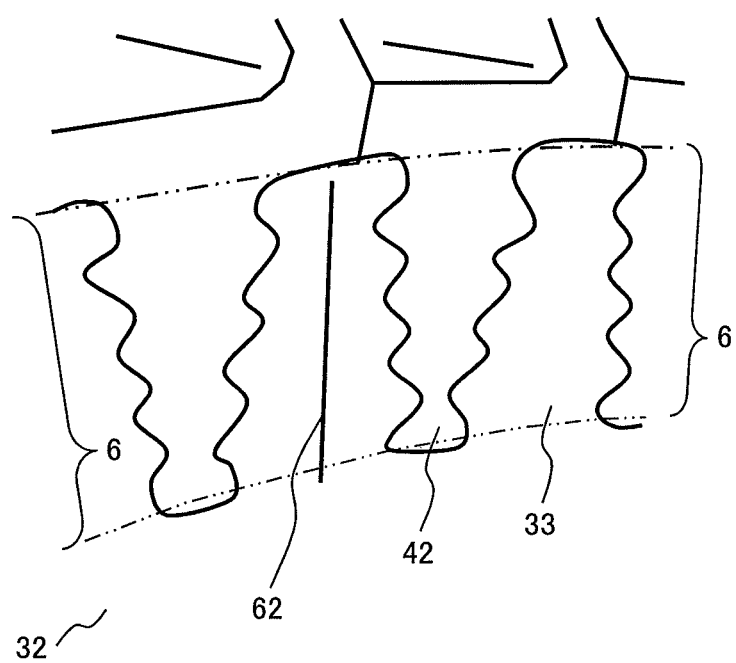
FIG. 5 shows a schematic view showing one example of a slit formed in the turbine rotor blade implanting portion, used for correcting the eddy current probe of the defect detection device of turbine rotor blade according to the embodiment of the present invention.

To correct the eddy current probe 71 constituting the defect detection device of turbine rotor blade, a correction slit 62 formed on the surface of the rotor blade implanting portion 6 of the turbine rotor blade 4 shown in FIG. 5 is used.

As shown in FIG. 5 as an example of the correction slit, the correction slit 62 is provided to one place on the surface of the rotor blade implanting portion 6 of the turbine rotor blade 4, 1 mm deep and 0.3 mm wide over the length of the inspection range in the radial direction; and using this correction slit 62, the sensitivity of the coil elements 78 is adjusted according to the output level of the indications of when each coil element 78 on the eddy current probe 71 passes over the correction slit 62 to correct the eddy current probe 71.

Note that, the eddy current probe 71 may be corrected by using the indications of when each coil element passes over the sets of blade grooves 42 and rotor grooves 33 without providing the correction slit 62 to the rotor blade implanting portion 6.

Next, in Step 105, a defect inspection scan is performed by the coil elements 78 installed on the front surface of the eddy current probe 71 for the inspection target of the rotor blade implanting portion 6 of the turbine rotor blade 4 rotating at low speed, by passing an eddy current to the surface of the rotor blade implanting portion 6 of the turbine blade 4, and the inspection data of a change in the electromagnetic induction generated on the surface of the rotor blade implanting portion 6 of the turbine rotor blade 4 obtained by the inspection scan, is obtained by the coil elements 78, the data of which is transmitted to the data analyzer 300.

Then, in Step 106, the data analyzer 300 performs calculation to remove a noise content created by the surrounding environment or the unsteadiness of the eddy current probe 71 during the scan, from the inspection data of a change in the electromagnetic induction obtained by the coil elements 78 of the eddy current probe 71.

Then, in Step 107, the inspection data of a change in the electromagnetic induction obtained by the coil elements 78 of the eddy current probe 71, from which the noise content is removed by the data analyzer 300, is processed to display an indication corresponding to the crack of a defect, such as the one shown in FIG. 3C, on a screen as the inspection result output 8.

Then, in the next Step 108, whether or not the indication 82 caused by a crack is identified on the indication screen is determined based on the inspection result output 8 on the indication screen displayed on the data analyzer 300.

In the determination of Step 108, when no indication 82 caused by a crack is identified, it is determined that no crack has occurred in the rotor blade implanting portion 6 of the turbine rotor blade 4, and the process moves on to Step 111 in which, the inspection is finished and the steam turbine remains on standby until the beginning of the next rated operation of the turbine.

In the determination of Step 108, however, when the indication 82 caused by a crack is identified, the process goes to the next Step 109 in which, the rotation of the steam turbine 1 by the external power motor is stopped. Then, the turbine casing 2 of the steam turbine 1 is opened to perform a detail inspection of the rotor blade implanting portion 6 of the turbine rotor blade 4.

Then, according to the result of this detail inspection of the rotor blade implanting portion 6 of the turbine rotor blade 4 in Step 109, the turbine rotor blade 4 is repaired or changed according to the situation in the next Step 110, then the process moves on to the above-mentioned Step 111 in which, the inspection is finished and the steam turbine remains on standby until the beginning of the next rated operation.

As clearly seen from the above descriptions, the defect detection device of turbine rotor blade and the method for detecting defect of turbine rotor blade can be achieved according to the embodiment of the present invention, which can accurately detect a defect occurring in the implanting portion of the turbine rotor blade even when the turbine rotor blades vibrate in the axial direction of the rotor as the rotor rotates, and can detect a defect occurring in the rotor blade implanting portion of the turbine rotor blade to be inspected without opening the turbine casing which requires a great deal of time and work.

Embodiment 2

Next, the defect detection device of turbine rotor blade and the method for detecting defect of turbine rotor blade according to a second embodiment of the present invention will be described with reference to FIG. 6.

Figure 6A:
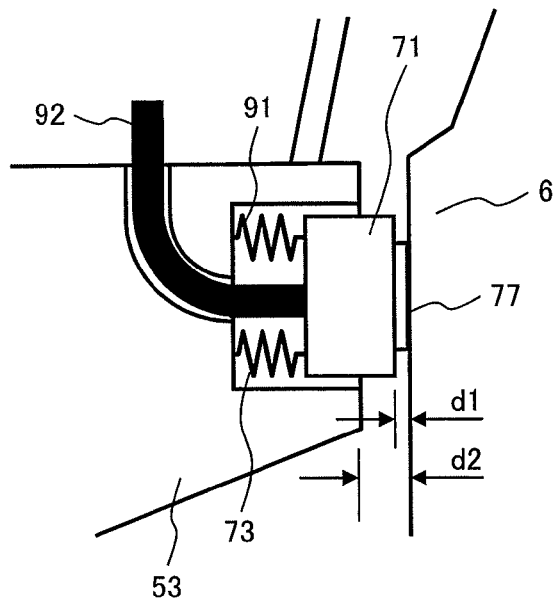
FIG. 6 shows structural views of an eddy current probe constituting a defect detection device for a turbine rotor blade according to a second embodiment of the present invention.
Figure 6B:
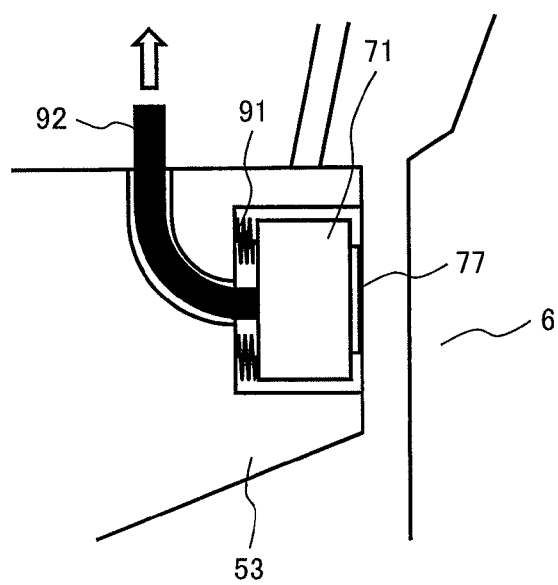

FIGS. 6A and 6B are structural views of the eddy current probe constituting the defect detection device of turbine rotor blade 7 according to the second embodiment of the present invention.

The eddy current probe 71 constituting the defect detection device of turbine rotor blade 7 according to the second embodiment of the present invention shown in FIGS. 6A and 6B has the same basic structure as the eddy current probe 71 constituting the defect detection device of turbine rotor blade according to the first embodiment shown in FIGS. 1 to 5, thus the description of the components common to the both will be omitted and only a different component will be discussed below.

In FIGS. 6A and 6B, the eddy current probe 71 constituting the defect detection device of turbine rotor blade 7 according to the second embodiment of the present invention is provided with a coil spring 91 between the back surface of the eddy current probe 71 and the recess 73 formed in the web 53 of the stationary blade diaphragm 5.

In place of the fiber rod 72, a cable 92 is connected to the eddy current probe 71. Note that, the steam turbine installed with the defect detection device of turbine rotor blade 7 according to the second embodiment is not shown in the figures.

In the defect detection device of turbine rotor blade 7 in the present embodiment, the elastic force of the coil spring 91 installed on the back surface of the eddy current probe 71 can be used to push the eddy current probe 71 against the surface of the rotor blade implanting portion 6 of the turbine rotor blade 4. This configuration gives an advantage that when the condition of a defect in the rotor blade implanting portion 6 of the turbine rotor blade 4 is to be inspected, the moving device 150 installed outside the turbine casing 2 is driven by an operation signal from the control device 200 or the defect detection device is manually operated from the outside of the turbine casing 2 only to allow the cable 92 to be moved forward through the casing hole 76 formed in the turbine casing 2, and there is no need of pushing force continuously applied to the eddy current probe 71.

In addition, even when a gap d2 between the web 53 of the stationary blade diaphragm 5 and the rotor blade implanting portion 6 of the turbine rotor blade 4 fluctuates during the scan of the rotor blade implanting portion 6 of the turbine rotor blade 4 by the eddy current probe 71, the contact state of the eddy current probe 71 can be maintained, that is, the defect detection device can flexibly respond to such condition.

Since the eddy current probe 71 is being pushed by the elastic force of the coil spring 91 installed between the eddy current probe 71 and the bottom surface of the recess 73 formed in the web 53 of the stationary blade diaphragm 5, when the condition of a defect in the rotor blade implanting portion 6 of the turbine rotor blade 4 is not to be inspected, the moving device 150 installed outside the turbine casing 2 can be driven by a command signal from the control device 200 or the defect detection device can be manually operated from the outside of the turbine casing 2 to pull the cable 92 through the casing hole 76 formed in the turbine casing 2 to store the eddy current probe 71 connected to the cable 92 inside the recess 73 formed in the web 53 of the stationary blade diaphragm 5 through the opening.

The present embodiment has an advantage that the cable 92 is not required to be partially rigid like the fiber rod 72 since the requirement of the cable 92 is to convey only pulling force from the outside of the turbine casing 2.

According to the embodiment of the present invention, the defect detection device of turbine rotor blade and the method for detecting defect of the turbine rotor blade can be achieved which can accurately detect a defect occurring in the turbine rotor blade implanting portion even when the turbine rotor blades vibrate in the axial direction of the rotor as the rotor rotates, and can detect a defect occurring in the rotor blade implanting portion of the turbine rotor blade to be inspected without opening the turbine casing which requires a great deal of time and work.

Embodiment 3

Next, the defect detection device of turbine rotor blade and the method for detecting defect of turbine rotor blade according to a third embodiment of the present invention will be described with reference to FIG. 7.

Figure 7A:
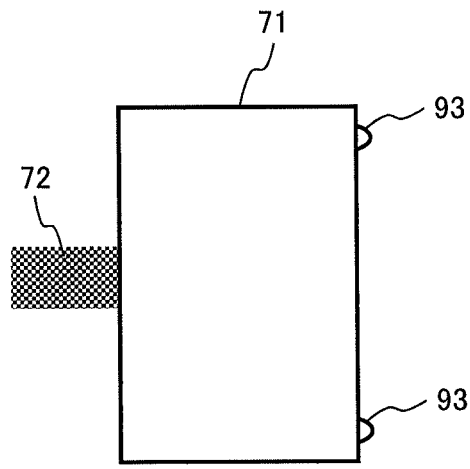
FIG. 7 shows structural views of an eddy current probe constituting a defect detection device for a turbine rotor blade according to a third embodiment of the present invention.
Figure 7B:
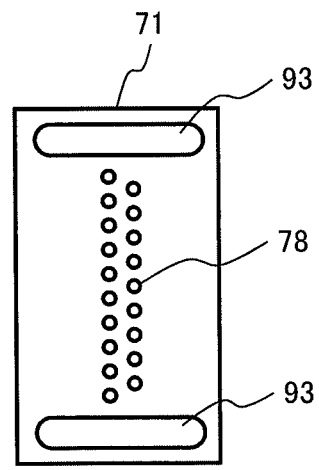
Figure 7C:
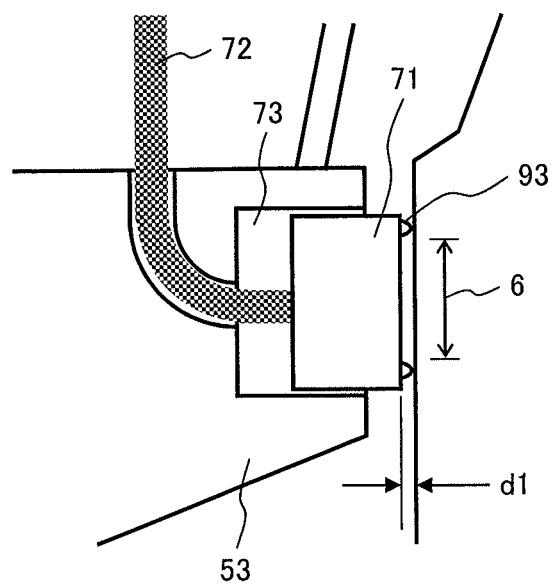

FIGS. 7A to 7C are structural views of the eddy current probe constituting the defect detection device of turbine rotor blade 7 according to the third embodiment of the present invention.

The eddy current probe 71 constituting the defect detection device of turbine rotor blade 7 according to the third embodiment of the present invention shown in FIGS. 7A to 7C has the same basic structure as the eddy current probe 71 constituting the defect detection device of turbine rotor blade 7 according to the first embodiment shown in FIGS. 1 to 5, thus the description of components common to the both will be omitted and only a different component will be described below.

In FIGS. 7A to 7C, sliding pads 93 are installed in place of the guide rollers 77 one above the other in the radial direction on the front surface of the eddy current probe 71 constituting the defect detection device of turbine rotor blade 7 according to the third embodiment of the present invention. Note that the steam turbine installed with the defect detection device of turbine rotor blade 7 according to the third embodiment is not shown in the figures.

In the present embodiment, these sliding pads 93 provided on the front surface of the eddy current probe 71 are formed with hard anti-abrasive material; minerals such as sapphire and ruby, a fluorine resin such as polytetrafluoroethylene, a peek resin, and the like may be used.

In the eddy current probe 71 in the present embodiment, even if the eddy current probe 71 abuts on the rotor blade implanting portion 6 of the turbine rotor blade 4 outside the range of the rotor blade implanting portion 6 of the turbine rotor blade 4 during the inspection for the condition of a defect in the rotor blade implanting portion 6 of the turbine rotor blade 4, the sliding pads 93 installed on the front surface of the eddy current probe 71 contact with and slide on the outside of the range of the rotor blade implanting portion 6 of the turbine rotor blade 4, so that no damage will occur to the rotor blade implanting portion 6 of the turbine rotor blade 4 due to the sliding of the sliding pads 93.

The eddy current probe 71 provided with the sliding pads 93 has an advantage that it has a simpler structure than the eddy current probe provided with the guide rollers.

According to the present embodiment, the defect detection device of turbine rotor blade and the method for detecting defect of turbine rotor blade can be achieved which can accurately detect a defect occurring in the turbine rotor blade implanting portion even when the turbine rotor blades vibrate in the axial direction of the rotor as the rotor rotates, and can detect a defect occurring in the rotor blade implanting portion of the turbine rotor blade to be inspected without opening the turbine casing which requires a great deal of time and work.

Embodiment 4

Next, the defect detection device of turbine rotor blade and the method for detecting defect of turbine rotor blade according to a fourth embodiment of the present invention will be described with reference to FIG. 8.

Figure 8A:
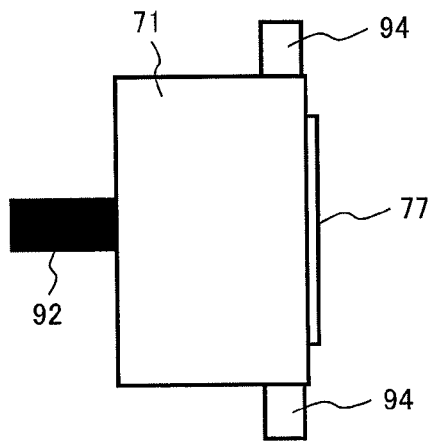
FIG. 8 shows structural views of an eddy current probe constituting a defect detection device for a turbine rotor blade according to a fourth embodiment of the present invention.
Figure 8B:
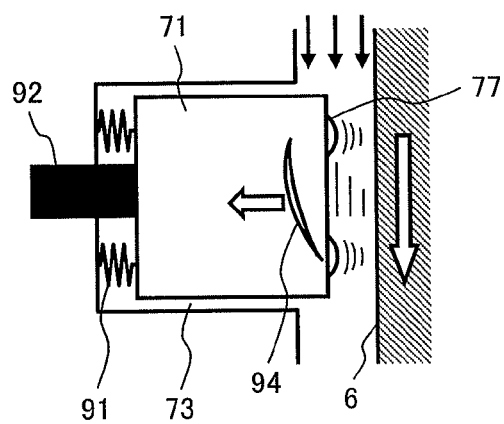
Figure 8C:
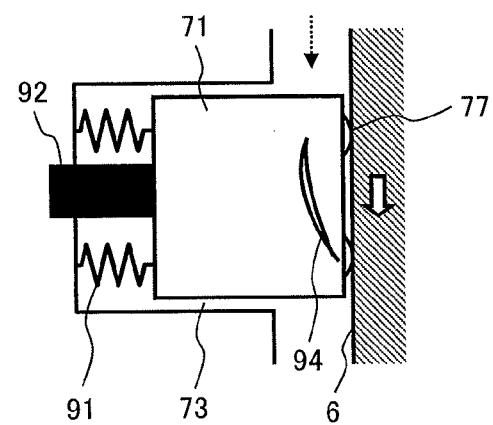

FIGS. 8A to 8C are structural views of the eddy current probe constituting the defect detection device of turbine rotor blade 7 according to the fourth embodiment of the present invention.

The eddy current probe 71 constituting the defect detection device of turbine rotor blade 7 according to the fourth embodiment of the present invention shown in FIGS. 8A to 8C has the same basic structure as the eddy current probe 71 constituting the defect detection device of turbine rotor blade 7 according to the first embodiment shown in FIGS. 1 to 5, thus the description of components common to the both will be omitted and only a different component will be described below.

In FIGS. 8A to 8C, an aerodynamic blade 94 is installed on the side surface of the eddy current probe 71 constituting the defect detection device of turbine rotor blade 7 according to the fourth embodiment of the present invention.

Note that the steam turbine installed with the defect detection device of turbine rotor blade 7 according to the fourth embodiment is not shown in the figures. In the present embodiment, the coil spring 91 is provided between the back surface of the eddy current probe 71 and the recess 73 formed in the web 53 of the stationary blade diaphragm 5, and the eddy current probe 71 is pushed against the surface of the rotor blade implanting portion 6 of the turbine rotor blade 4 using the elastic force of the coil spring 91. Furthermore, the cable 92 is connected to the eddy current probe 71.

In the eddy current probe 71 having the above structure, when the steam turbine is rotating at high-speed such as when it is in the rated operation, the aerodynamic blade 94 of the eddy current probe 71 receives strong fluid force in the circumferential direction, which generates lift for moving the eddy current probe 71 away from the rotor blade implanting portion 6 of the turbine rotor blade 4, opposing the reaction force of the coil spring 91, thus a damage to the eddy current probe 71 can be prevented.

When the steam turbine is rotating at low speed such as when the condition of a defect in the rotor blade implanting portion 6 of the turbine rotor blade 4 is to be inspected, the fluid force in the circumferential direction will be too small to generate the lift received by the aerodynamic blade 94 of the eddy current probe 71, allowing the eddy current probe 71 to be pushed against the rotor blade implanting portion 6 of the turbine rotor blade 4 by the action of the coil spring 91.

This configuration has an advantage that, it is not necessary to operate the cable 92 from the outside of the turbine casing 2 to move the eddy current probe 71 away from the rotor blade implanting portion 6 of the turbine rotor blade 4 when the inspection of the condition of a defect in the rotor blade implanting portion 6 of the turbine rotor blade 4 is not to be performed.

According to the embodiment in the present invention, the defect detection device of turbine rotor blade and the method for detecting defect of turbine rotor blade can be achieved which can accurately detect a defect occurring in the turbine rotor blade implanting portion even when the turbine rotor blades vibrate in the axial direction of the rotor as the rotor rotates, and can detect a defect occurring in the rotor blade implanting portion of the turbine rotor blade to be inspected without opening the turbine casing which requires a great deal of time and work.

Embodiment 5

Next, the defect detection device of turbine rotor blade and the method for detecting defect of turbine rotor blade according to a fifth embodiment of the present invention will be described with reference to FIG. 9.

Figure 9A:
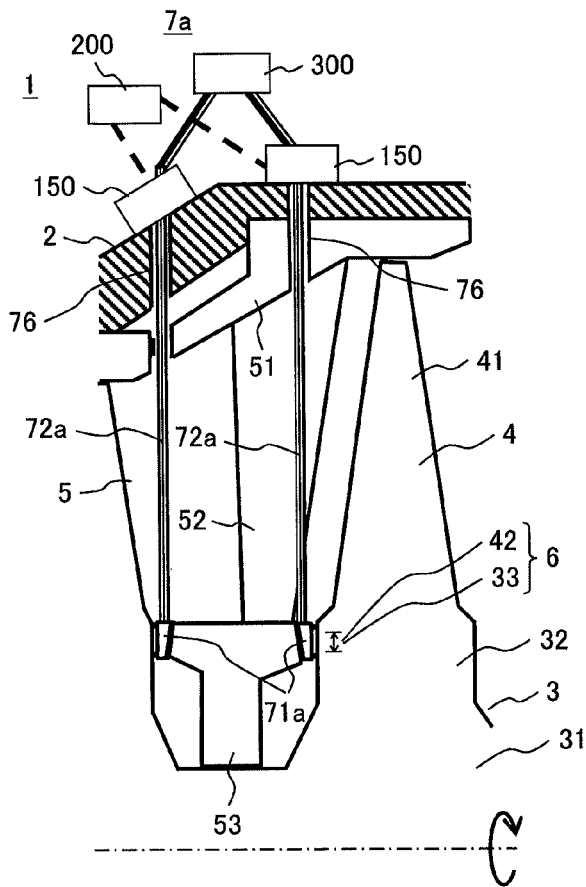
FIG. 9 shows a structural view of an eddy current probe constituting a defect detection device for a turbine rotor blade according to a fifth embodiment of the present invention, and partial cross-sectional views of a steam turbine installed with the defect detection device of turbine rotor blade.

FIG. 9A is a partial cross-sectional view of a steam turbine installed with a turbine rotor blade defect detection device 7a according to the fifth embodiment of the present invention.

Figure 9B:
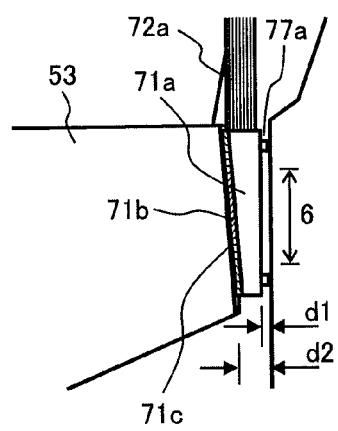
Figure 9C:
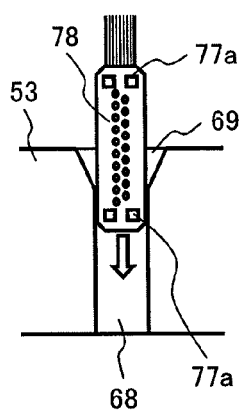
Figure 9D:
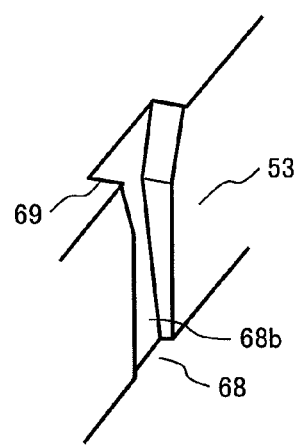

FIGS. 9B to 9D are structural views of an eddy current probe 71a constituting part of the defect detection device of turbine rotor blade 7a according to the fifth embodiment of the present invention.

The defect detection device of turbine rotor blade 7a according to the fifth embodiment of the present invention shown in FIGS. 9A to 9D has the same basic structure as the defect detection device of turbine rotor blade 7 according to the first embodiment shown in FIGS. 1 to 5, thus the description of components common to the both will be omitted and only a different component will be described below.

As shown in FIG. 9C, the eddy current probe 71a provided to the defect detection device of turbine rotor blade 7a according to the fifth embodiment of the present invention employs a slim shape having a narrower width than the casing hole 76 formed in the turbine casing 2.

As shown in FIGS. 9B and 9C, the upper end of the eddy current probe 71a in the radial direction is coupled with a hard access rod 72a having inside a signal line for transmitting a signal detected by the eddy current probe 71a.

Furthermore, guide rollers 77a installed on the front surface of the eddy current probe 71a are arranged above and below the coil elements 78 in the radial direction, two at each side; which configuration allows the eddy current probe 71a to be made slim in the circumferential direction.

In the defect detection device of turbine rotor blade 7a according to the fifth embodiment of the present invention as shown in FIG. 9A, instead of having the web hole 74 and the recess 73 formed in the web 53 of the stationary blade diaphragm 5 for the defect detection device of turbine rotor blade 7 according to the first embodiment shown in FIG. 1, a fixing groove 68 for storing and fixing the eddy current probe 71a, opened to the radial direction of the stationary blade diaphragm 5 is provided to the web 53 of the stationary blade diaphragm 5, as shown in FIGS. 9C and 9D; and the upper end of this fixing groove 68 in the radial direction has an opening 69.

In the defect detection device of turbine rotor blade 7a according to the fifth embodiment, when the condition of a defect in the rotor blade implanting portion 6 of the turbine rotor blade 4 is to be inspected, the moving device 150 installed outside the turbine casing 2 is driven by a command signal from the control device 200 or the defect detection device is manually operated from the outside of the turbine casing 2 to insert the eddy current probe 71a and the access rod 72a inside from the outside of the turbine casing 2 through the casing hole 76 formed in the turbine casing 2, and the eddy current probe 71a is moved in the space formed between the adjoining stationary blades 52 installed in the stationary blade diaphragm 5, and inserted and fixed to the fixing groove 68 formed in the web 53 of the stationary blade diaphragm 5.

Then, the guide rollers 77a on the front surface of the eddy current probe 71a are made to abut on the rotor blade implanting portion 6 of the turbine rotor blade 4 to be inspected, an eddy current is passed to the surface of the rotor blade implanting portion 6 of the turbine rotor blade 4 by the coil elements 78 installed on the front surface of the eddy current probe 71a, and a change in the electromagnetic induction occurred on the surface of the rotor blade implanting portion 6 of the turbine rotor blade 4 is detected by the coil elements 78; in this way, the condition of a defect in the rotor blade implanting portion 6 of the turbine rotor blade 4 is inspected in the same manner as using the eddy current probe 71 according to the previously-described embodiment.

Since the eddy current probe 71a has a slim shape with the width narrower than the casing hole 76 formed in the turbine casing 2, it can be moved in and out of the turbine casing 2 through the casing hole 76.

The back of the eddy current probe 71a is a tapered surface 71b, as shown in FIG. 9B, to make the thickness of the probe thinner toward the end in the axial direction, and the corresponding portion of the fixing groove 68 formed in the web 53 of the stationary blade diaphragm 5 for storing the eddy current probe 71a also has a tapered surface 68b with the same angle.

These tapered configurations can resolve the variation in the gaps d2 between the web 53 of the stationary blade diaphragm 5 and the rotor blade implanting portion 6 of the turbine rotor blade 4 by adjusting the depth of insertion of the eddy current probe 71a into the fixing groove 68 formed in the web 53.

In addition, an elastic cushion 71c is provided to the tapered surface 71b on the back surface of the eddy current probe 71a to absorb fluctuations in the gap d2 during scanning. Solid rubber, hollow rubber, leaf spring, or organic foam can be used as a material for the cushion 71c.

After the inspection of the condition of a defect in the rotor blade implanting portion 6 of the turbine rotor blade 4 is completed, the moving device 150 installed outside the turbine casing 2 is driven by a command signal from the control device 200 or the defect detection device is manually operated from the outside of the turbine casing 2 to pull the eddy current probe 71a and the access rod 72a out of the turbine casing 2 to completely take out the eddy current probe 71a to the outside of the turbine casing 2.

The eddy current probe 71a has an advantage that it can be taken out to the outside of the turbine casing 2 for safe storage during the period when the condition of a defect in the rotor blade implanting portion 6 of the turbine rotor blade 4 is not to be inspected, which increases the reliability of the defect detection device of turbine rotor blade 7a.

According to the embodiment of the present invention, the defect detection device of turbine rotor blade and the method for detecting defect of the turbine rotor blade can be achieved which can accurately detect a defect occurring in the turbine rotor blade implanting portion even when the turbine rotor blades vibrate in the axial direction of the rotor as the rotor rotates, and can detect a defect occurring in the rotor blade implanting portion of the turbine rotor blade to be inspected without opening the turbine casing which requires a great deal of time and work.

INDUSTRIAL APPLICABILITY

The present invention can be applied not only to the defect detection device of turbine rotor blade and the method for detecting defect of the turbine rotor blade for detecting a defect occurring in the implanting portion of the turbine rotor blade in a steam turbine, but also to those for the other turbine rotor blades as long as the eddy current probe can withstand the environment they offer.

The invention claimed is:

1. A defect detection device for a turbine rotor blade having a turbine rotor blade implanting portion constructed by fitting a set of rotor grooves formed on a rotor disc portion of a turbine rotor and a set of blade grooves formed on a root portion of the turbine rotor blade, wherein the turbine rotor is rotatably installed inside a turbine casing, and around an outer circumference of the turbine rotor, a plurality of turbine rotor blades are annularly arranged, and wherein a stationary blade diaphragm, where a plurality of stationary blades are annularly arranged adjacent to the turbine rotor blades, is provided with an annular web in an inner circumference side thereof, and an outer circumference side thereof is fixed with the turbine casing, comprising:

a movable eddy current probe for inspecting a state of the turbine rotor blade implanting portion, installed in a recess provided in a side surface of the annular web of the stationary blade diaphragm, facing the turbine rotor blade implanting portion;

a fiber rod provided with a signal line for transmitting a signal detected by the eddy current probe, connected to the eddy current probe, and set up to be movable through a hole formed in the turbine casing and an air gap formed in the stationary blade of the stationary blade diaphragm, the fiber rod being a flexible fiber rod and inserted in the air gap formed in the stationary blade of the stationary blade diaphragm to be bent in a hole in the annular web so as to change a direction of the fiber rod to axial direction of the turbine rotor, so that the eddy current probe connected to the fiber rod is moved toward or away from the turbine rotor blade implanting portion; and a data analyzer for determining a condition of a defect that has occurred in the turbine rotor blade implanting portion based on the detection signal of the turbine rotor blade implanting portion detected by the eddy current probe transmitted through the fiber rod;

whereby the turbine rotor blade implanting portion is inspected by the eddy current probe under a condition that the turbine rotor is rotatably installed inside of the turbine casing.

2. The defect detection device for the turbine rotor blade according to claim 1, wherein a moving device for moving the rod and a control device for controlling an operation of the moving device are installed outside the turbine casing.

3. The defect detection device for the turbine rotor blade according to claim 1, wherein an aerodynamic blade is provided to the eddy current probe to receive fluid force in a circumferential direction of the rotating turbine rotor so as to generate lift for the eddy current probe in the direction toward the stationary blade diaphragm to move the eddy current probe away from the turbine rotor blade implanting portion.

4. The defect detection device for the turbine rotor blade according to claim 1, wherein a probe correction slit is formed in at least one location on the surface of the turbine rotor blade implanting portion.

5. The defect detection device for the turbine rotor blade according to claim 1, wherein a first coil element for passing an eddy current to a surface of the turbine rotor blade implanting portion, a second coil element for detecting a change in electromagnetic induction generated on the surface of the turbine rotor blade implanting portion by the eddy current passed from the first coil element, and a sliding mechanism for sliding upon touching the turbine rotor blade implanting portion are provided on a surface of the eddy current probe facing the turbine rotor blade implanting portion.

6. The defect detection device for the turbine rotor blade according to claim 5, wherein the sliding mechanism provided to the eddy current probe is installed so as to protrude toward the turbine rotor blade further out than the coil elements.

7. The defect detection device for the turbine rotor blade according to claim 5, wherein a roller is provided as the sliding mechanism.

8. The defect detection device for the turbine rotor blade according to claim 5, wherein a protrusion made of metal, ceramic, or resin is provided as the sliding mechanism.

9. The defect detection device for the turbine rotor blade according to claim 5, wherein a plurality of coil elements are arranged for each kind of the coil elements provided on the surface of the eddy current probe facing the turbine rotor blade implanting portion.

10. The defect detection device for the turbine rotor blade according to claim 1, wherein the eddy current probe is connected to the recess through an elastic body, and elastic force of the elastic body is used to push the eddy current probe against the turbine rotor blade implanting portion.

11. A defect detection device for a turbine rotor blade having a turbine rotor blade implanting portion constructed by fitting a set of rotor grooves formed on a rotor disc portion of a turbine rotor with a set of blade grooves formed on a root portion of the turbine rotor blade, wherein the turbine rotor is rotatably installed inside a turbine casing, and around an outer circumference of the turbine rotor, a plurality of turbine rotor blades are annularly arranged, and wherein a stationary blade diaphragm, where a plurality of stationary blades are annularly arranged adjacent to the turbine rotor blades, is provided with an annular web in an inner circumference side thereof, and an outer circumference side thereof is fixed with the turbine casing, comprising:

an eddy current probe for detecting a state of the turbine rotor blade implanting portion, the eddy current probe having a slim shape with a width narrower than a casing hole formed in the turbine casing;

a groove portion for inserting the eddy current probe, provided on a side surface of the annular web of the stationary blade diaphragm facing the turbine rotor blade implanting portion, opened toward a radial direction of the stationary blade diaphragm, the groove portion having a tapered bottom surface for making the groove shallower toward a rotor shaft, wherein the tapered bottom surface abuts another tapered surface formed on a stationary blade diaphragm side of the eddy current probe so that the eddy current probe is movable toward or away from the turbine rotor blade implanting portion by a sliding action of the tapered bottom surface of the groove portion and the other tapered surface of the eddy current probe;

a rod provided with a signal line for transmitting a signal detected by the eddy current probe, connected to the eddy current probe, and set up to be movable through a hole formed in the turbine casing and a space between the stationary blades installed in the stationary blade diaphragm to move the eddy current probe connected to the rod toward or away from the turbine rotor blade implanting portion; and a data analyzer for determining a condition of a defect that has occurred in the turbine rotor blade implanting portion based on the detection signal of the turbine rotor blade implanting portion detected by the eddy current probe transmitted through the fiber rod;

whereby the turbine rotor blade implanting portion is inspected by the eddy current probe under a condition that the turbine rotor is rotatably installed inside of the turbine casing.

12. The defect detection device for the turbine rotor blade according to claim 11, wherein a moving device for moving the rod and a control device for controlling an operation of the moving device are installed outside the turbine casing.

13. The defect detection device for the turbine rotor blade according to claim 11, wherein a first coil element for passing an eddy current to a surface of the turbine rotor blade implanting portion, a second coil element for detecting a change in electromagnetic induction generated on the surface of the turbine rotor blade implanting portion by the eddy current passed from the first coil element, and a sliding mechanism for sliding upon touching the turbine rotor blade implanting portion are provided on a surface of the eddy current probe facing the turbine rotor blade implanting portion.

14. The defect detection device for the turbine rotor blade according to claim 11, wherein other elastic body is installed on a surface of a stationary blade diaphragm side of the eddy current probe.

15. The defect detection device for the turbine rotor blade according to claim 14, wherein the other elastic body installed on the surface of the stationary blade diaphragm side of the eddy current probe is formed with solid rubber, hollow rubber, leaf spring or organic foam.

16. A method for detecting a defect of a turbine rotor blade having a turbine rotor blade implanting portion constructed by fitting a set of rotor grooves formed on a rotor disc portion of a turbine rotor with a set of blade grooves formed on each root portion of a plurality of turbine rotor blades annularly arranged around an outer circumference of the turbine rotor rotatably installed in a turbine casing, comprising the steps of:

movably setting up an eddy current probe in a recess formed on a side surface of a web facing the turbine rotor blade implanting portion, the web being among multiple webs provided to an inner circumference side of a stationary blade diaphragm where a plurality of stationary blades are annularly arranged;

operating a fiber rod provided with a signal line for transmitting a signal detected by the eddy current probe, connected to the eddy current probe, from outside of the turbine casing to move through a hole formed in the turbine casing and an air gap formed in the stationary blade of the stationary blade diaphragm when a state of a defect that has occurred in the turbine rotor blade implanting portion is to be inspected, the fiber rod being a flexible fiber rod and inserted in the air gap formed in the stationary blade of the stationary blade diaphragm to be bent in a web hole so as to change a direction of the fiber rod to axial direction of the turbine rotor, so that the eddy current probe connected to the fiber rod is moved toward or away from the turbine blade implanting portion;

moving the eddy current probe connected to the moving fiber rod toward or away from the turbine rotor blade implanting portion to inspect a state of the turbine rotor blade implanting portion using the eddy current probe; and determining a condition of the defect that has occurred in the turbine rotor blade implanting portion based on the detection signal of the state of the turbine rotor blade implanting portion detected by the eddy current probe transmitted through the fiber rod;

whereby the turbine rotor blade implanting portion is inspected by the eddy current probe under a condition that the turbine rotor is rotatably installed inside of the turbine casing.

17. The method for detecting the defect of the turbine rotor blade according to claim 16, wherein a first coil element installed on a surface of the eddy current probe passes an eddy current to a surface of the turbine rotor blade implanting portion, a second coil element installed on the surface of the eddy current probe detects a change in electromagnetic induction generated on the surface of the turbine rotor blade implanting portion by the eddy current passed from the first coil element, and the condition of the defect occurred in the turbine rotor blade implanting portion is determined based on the detection signal of the state of the turbine rotor blade implanting portion, which is a detected value of the change in the electromagnetic induction.

18. A method for detecting a defect of a turbine rotor blade having a turbine rotor blade implanting portion constructed by fitting a set of rotor grooves formed on a rotor disc portion of a turbine rotor with a set of blade grooves formed on each root portion of a plurality of turbine rotor blades annularly arranged around an outer circumference of the turbine rotor rotatably installed in a turbine casing, comprising the steps of:

removably setting up an eddy current probe in a groove portion formed on a side surface of a web, facing the turbine rotor blade implanting portion, opened toward a radial direction of a stationary blade diaphragm, the web being among multiple webs provided to an inner circumference side of the stationary blade diaphragm where a plurality of stationary blades are annularly arranged;

inserting a fiber rod provided with a signal line for transmitting a signal detected by the eddy current probe, connected to the eddy current probe, from outside of the turbine casing to move through a hole formed in the turbine casing and a space between the stationary blades installed in the stationary blade diaphragm when a state of a defect that has occurred in the turbine rotor blade implanting portion is to be inspected, the eddy current probe having a slim shape with a width narrower than the casing hole formed in the turbine casing;

inserting the eddy current probe connected to the moving rod into the groove portion formed on the side surface of the web of the stationary blade diaphragm and positioning the eddy current probe closer to the turbine rotor blade implanting portion to inspect the state of the turbine rotor blade implanting portion using the eddy current probe; and determining a condition of the defect that has occurred in the turbine rotor blade implanting portion based on a detection signal of the state of the turbine rotor blade implanting portion detected by the eddy current probe transmitted through the fiber rod;

whereby the turbine rotor blade implanting portion is inspected by the eddy current probe under a condition that the turbine rotor is rotatably installed inside of the turbine casing.

19. The method for detecting the defect of the turbine rotor blade according to claim 18, wherein a first coil element installed on a surface of the eddy current probe passes an eddy current to a surface of the turbine rotor blade implanting portion, a second coil element installed on the surface of the eddy current probe detects a change in electromagnetic induction generated on the surface of the turbine rotor blade implanting portion by the eddy current passed from the first coil element, and the condition of the defect that has occurred in the turbine rotor blade implanting portion is determined based on the detection signal of the state of the turbine rotor blade implanting portion, which is a detected value of the change in the electromagnetic induction.

* * * * *